(12) United States Patent
Baron

(10) Patent No.: US 7,066,899 B2
(45) Date of Patent: Jun. 27, 2006

(54) CAST COVER AND METHOD OF USE

(76) Inventor: Sally J. Baron, 3645 Mission Mesa Way, San Diego, CA (US) 92120

( * ) Notice: Subject to any disclaimer, the term of this patent is extended or adjusted under 35 U.S.C. 154(b) by 0 days.

(21) Appl. No.: 10/969,546

(22) Filed: Oct. 20, 2004

(65) Prior Publication Data

US 2006/0084896 A1    Apr. 20, 2006

(51) Int. Cl.
*A61F 5/00* (2006.01)
(52) U.S. Cl. .......................... 602/3; 128/856
(58) Field of Classification Search ............ 602/3, 602/21; 2/161.7, 20, 59, 239, 62, 160; D24/190; D2/610; 128/856
See application file for complete search history.

(56) References Cited

U.S. PATENT DOCUMENTS

| | | | |
|---|---|---|---|
| 2,334,206 A | 11/1943 | Knohl | |
| 3,327,705 A | 6/1967 | Miller et al. | |
| 3,785,374 A * | 1/1974 | Lipson | 602/3 |
| 4,139,003 A | 2/1979 | Little et al. | |
| 4,346,699 A * | 8/1982 | Little et al. | 602/3 |
| 4,363,317 A * | 12/1982 | Broucek | 602/3 |
| D270,001 S * | 8/1983 | Felton | D24/192 |
| 4,646,727 A | 3/1987 | Chambers | |
| D294,736 S | 3/1988 | Thygesen | |
| 4,727,864 A | 3/1988 | Wiesenthal et al. | |
| D295,559 S | 5/1988 | Kristensen et al. | |
| 4,966,135 A * | 10/1990 | Renfrew | 602/3 |
| 4,986,265 A | 1/1991 | Caponi | |
| 5,000,171 A | 3/1991 | Hofer | |
| 5,063,919 A * | 11/1991 | Silverberg | 602/3 |
| 5,070,541 A * | 12/1991 | Goss | 2/16 |
| 5,070,630 A | 12/1991 | Edmundson | |
| 5,088,484 A | 2/1992 | Freeman et al. | |
| 5,402,536 A * | 4/1995 | Matthews | 2/16 |
| 5,882,320 A | 3/1999 | Peterson | |
| D410,088 S | 5/1999 | Rutledge et al. | |
| D415,282 S * | 10/1999 | Rutledge et al. | D24/190 |
| 6,047,403 A * | 4/2000 | Juozaitis | 2/61 |
| 6,126,621 A * | 10/2000 | Aceves | 602/3 |
| 6,298,496 B1 | 10/2001 | Evans | |
| 6,450,982 B1 | 9/2002 | Peterson | |
| D484,604 S | 12/2003 | Tramel et al. | |
| 6,916,301 B1 * | 7/2005 | Clare | 602/3 |
| 2003/0191419 A1 | 10/2003 | Melin et al. | |
| 2003/0191424 A1 | 10/2003 | Skinner | |

* cited by examiner

*Primary Examiner*—Henry Bennett
*Assistant Examiner*—Camtu Nguyen
(74) *Attorney, Agent, or Firm*—Stephen C. Beuerle; Procopio Cory Hargreaves & Savitch LLP

(57) ABSTRACT

An orthopedic cast cover for covering an orthopedic cast of a user includes a tubular portion for covering the orthopedic cast; a distal portion including a thumb hole for receiving a thumb of the user and an oval finger opening for receiving fingers of the user; and finger separators spanning the oval finger opening and extending linearly between the fingers in V-shaped portions formed between the fingers.

15 Claims, 2 Drawing Sheets

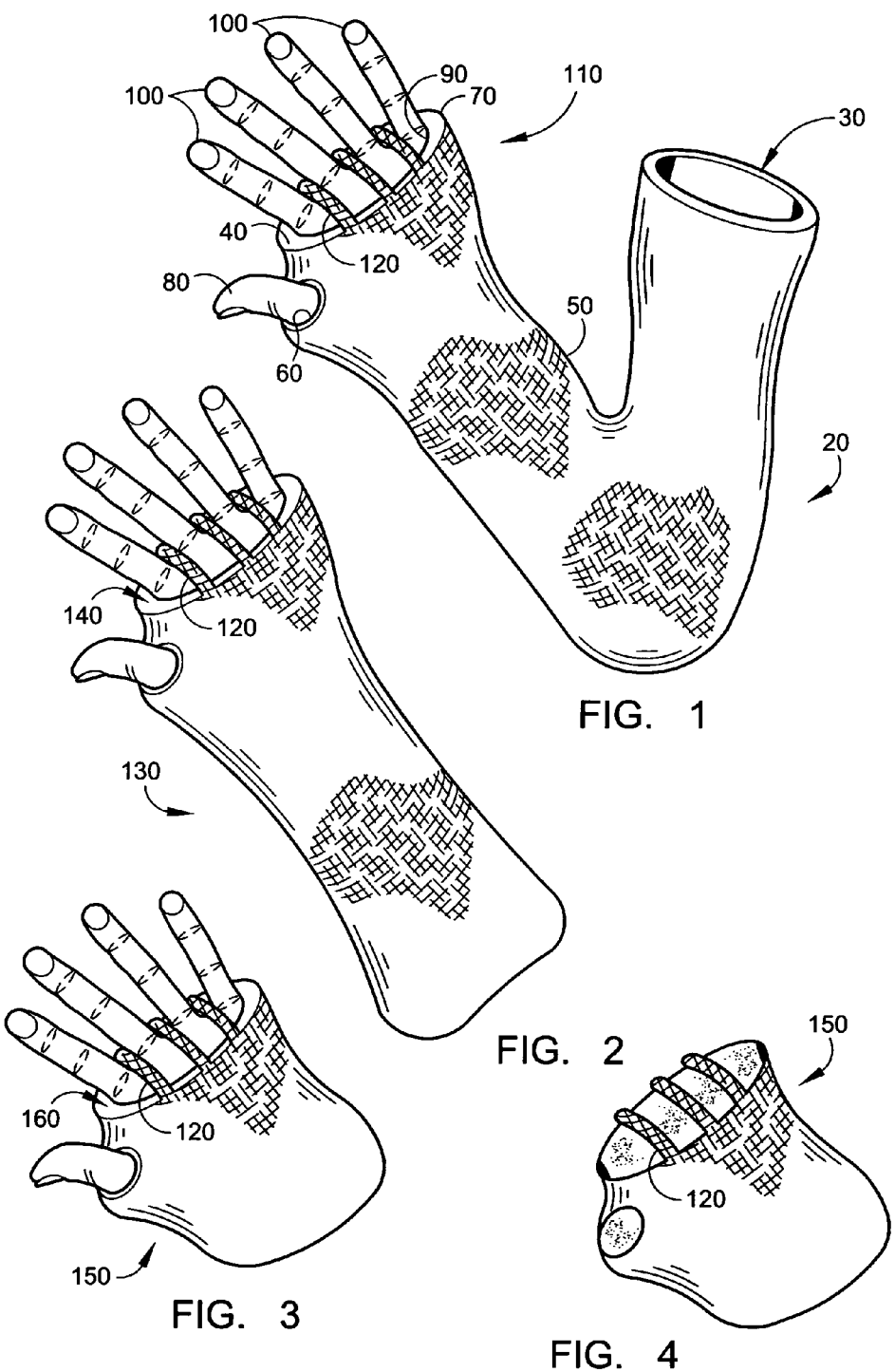

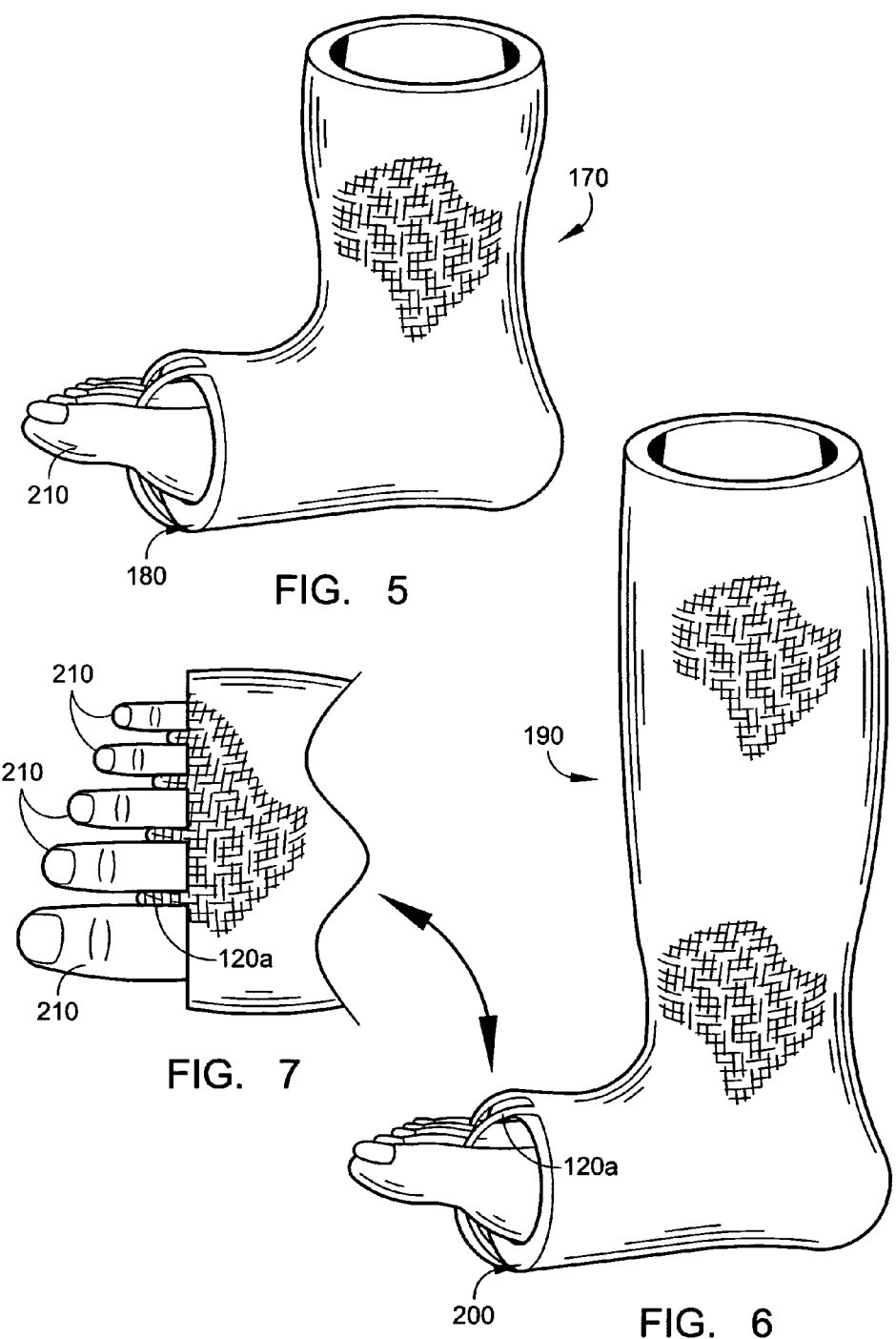

CAST COVER AND METHOD OF USE

FIELD OF THE INVENTION

The present invention is in the field of orthopedic cast covers.

BACKGROUND OF THE INVENTION

Orthopedic cast covers have been developed in the past to cover and protect wrist, short-arm, long-arm, short-leg, and long-leg casts. A big problem for cast wearers is their need to have a cast changed because the cast has become dirty (or the cast color does not match other clothes) and the wearer has a special event to attend, etc. It costs $150.00 or more to change the cast, and the process is time-consuming and inconvenient for both physicians and patients.

Another problem with orthopedic casts is that the existing colored fiberglass cast material causes pulls in clothing material and scratches on furniture.

A problem with cast covers of the past is that they do not prevent moisture and contaminant build-up between the fingers or toes. As a result, skin lesions develop in the V-shaped areas between the fingers or toes.

SUMMARY OF THE INVENTION

The cast cover of the present invention eliminates the need to change casts. The cast cover protects the cast and is decorative. The protective nature of the cast cover prevents pulls in clothing and scratches on furniture. Cast covers with different colors/designs can be worn for different occasions. The cast cover can be easily slipped on, over a cast, and easily removed from the cast. Because the cast cover is washable, the cast cover can be frequently cleaned. Separators at an end of the cast cover prevent moisture and contaminant build-up between the fingers (or toes).

Another aspect of the present invention involves an orthopedic cast cover for covering an orthopedic cast of a user. The orthopedic cast cover includes a tubular portion for covering the orthopedic cast; a distal portion including a thumb hole for receiving a thumb of the user and an oval finger opening for receiving fingers of the user; and finger separators spanning the oval finger opening and extending linearly between the fingers in V-shaped portions formed between the fingers.

A further aspect of the invention involves a method of using an orthopedic cast cover for covering an orthopedic cast of a user. The method includes the steps of providing an orthopedic cast cover including a tubular portion for covering the orthopedic cast, a distal portion including a thumb hole for receiving a thumb of the user and an oval finger opening for receiving fingers of the user, and finger separators spanning the oval finger opening and extending linearly between the fingers in V-shaped portions formed between the fingers; inserting at least one of an arm and wrist cast through the orthopedic cast cover so that the finger separators extend linearly between the fingers in the V-shaped portions formed between the fingers of the user's hand; and absorbing moisture and soil in the V-shaped sections between the fingers with the finger separators, thereby inhibiting development of skin lesions between the fingers.

Further objects and advantages will be apparent to those skilled in the art after a review of the drawings and the detailed description of the preferred embodiments set forth below.

BRIEF DESCRIPTION OF THE DRAWINGS

FIG. 1 is a perspective view of an embodiment of a long-arm cast cover with a long-arm cast and user's fingers shown.

FIG. 2 is a perspective view of an embodiment of a short-arm cast cover with a short-arm cast and user's fingers shown.

FIG. 3 is a perspective view of an embodiment of a wrist cast cover with a wrist cast and user's fingers shown.

FIG. 4 is a perspective view of the wrist cast cover shown in FIG. 3 without the wrist cast and the user's fingers shown.

FIG. 5 is a perspective view of an embodiment of a short-leg cast cover with a short-leg cast and the user's toes shown.

FIG. 6 is a perspective view of an embodiment of a long-leg cast cover with a long-leg cast and the user's toes shown.

FIG. 7 is a top plan view of the cast cover of FIG. 6 with the user's toes shown.

DETAILED DESCRIPTION OF PREFERRED EMBODIMENTS

With reference to FIGS. 1–4, and initially FIG. 1, an orthopedic cast cover (hereinafter "cover") 20 constructed in accordance with an embodiment of the invention will now be described. The cover 20 is a long-arm cast cover and is shown applied over a long-arm cast 30 with a user's fingers shown extending from a distal end 40 of the cast 30.

The cover 20 is made of a washable, stretchable material that slips over the cast 30. The cover 20 has a generally tubular portion ("tube") 50 that serves as a protective and decorative covering. The cover 20 may include a finished binding for the thumb, around the fingers, at a middle part of the limb, and at an upper part of the limb. The binding may be elastic. A thumb hole 60 is formed near a distal portion 70 of the cover 20. Preferably, the thumb hole 60 is situated so that the cover 20 fits thumb 80 between the first and second knuckle of the thumb 80. An oval finger opening 90 is adjacent the thumb hole 60 and receives fingers 100 of user's hand 110. Linear elongated tubular finger separators 120 separate the fingers 100 from each other. The separators 120 have a cylindrical configuration and each separator extends between two opposite points on the circumference of the finger opening 90, parallel with each other, and spanning the opening 90. The separators 120 are made of an absorbent material and may include an elastic material therein.

When the cover 20 is properly pulled over the cast 30, each separator 120 respectively fits at the base of the V-shaped section between fingers 100. The tubular separators 120 are absorbent, absorbing moisture in the V-shaped sections between fingers 100. This protects the skin in the V-shaped sections, at the base of the fingers 100, from moisture and soil, thereby inhibiting development of skin lesions between the fingers 100.

In alternative embodiments of the covers 20 (and the covers described below), the covers 20 are formed from various decorative materials, color schemes, designs, patterns, themes, and/or logos. This allows the wearer to coordinate outfits and include the cast 30. For example, for females, the cover 20 may have feminine themes. For males, the cover 20 may have sports-related or other male themes. For children, the cover 20 may have children themes. The cover 20 may come in dressy models and/or casual models. Designs on the covers 20 may be added to the covers 20 with the use of screen printing. The cast covers 20 may come in different sizes (e.g., man size, woman size, child size). The covers 20 include an outer layer/liner and an inner layer/ liner. The liners may be made of, for example, but not by way of limitation, one or more of cotton, Neoprene® material, Spandex® material, and Lycra® material. Cold-weather versions of the covers 20 may include one or more additional linings (e.g., a cotton flannel lining) to increase warmth for the wearer.

The cover 20 is easily slipped on over the cast by inserting one's hand through the cover 20 similar to putting one's hand through a long sleeve of a jacket, shirt, sweatshirt or the like. One's fingers are inserted through the distal portion 70 of the cover 20 in a manner similar to putting on a glove so that the separators 120 are disposed between the user's fingers 100 and the user's thumb 80 is disposed through the thumb hole 60. After use, the cover 20 is removed, laundered, and stored.

FIGS. 2–4 show alternative embodiments of the cover. For example, FIG. 2 illustrates an embodiment of a short-arm cast cover 130 for covering a short-arm cast 140; and FIG. 3 illustrates an embodiment of a wrist cast cover 150 for covering a wrist cast 160. FIG. 4 illustrates the wrist cast cover 150 without the cast 160 and the user's fingers 100 shown. Aside from the covers 130, 150 having different lengths from the cover 20, the covers 130, 150 include separators 120 and other features similar to those of the cover 20. The covers 20, 130, 150 preferably have a single configuration that fit casts for both the left arm/wrist and the right arm/wrist. Alternatively, the covers 20, 130, 150 may have separate configurations for the left arm/wrist and the right arm/wrist.

In alternative embodiments of the cover 20, 130, 150, the cover 20, 130, 150 may include a complete glove/mitten for the hand/fingers for cold weather protection.

FIGS. 5–7 show further embodiments of cast covers that may be used for short-leg, and/or long-leg casts. For example, FIG. 5 illustrates an embodiment of a short-leg cast cover 170 for covering a short-leg cast 180; and FIG. 6 illustrates an embodiment of a long-leg cast cover 190 for covering a long-leg cast 200. As illustrated best in FIG. 7, the covers 170, 190 include separators 120a similar to the separators 120 described above. The tubular separators 120a are absorbent, absorbing moisture in the V-shaped sections between toes 210. This protects the skin in the V-shaped sections, at the base of the toes 210, from moisture and soil, thereby inhibiting development of skin lesions between the toes 210.

In alternative embodiments of the covers 170, 190, the cover 170, 190 may not include the separators 120a or the cover 170, 190 may include a complete sock to cover the toes 210.

The covers 170, 190 preferably have a single configuration that fit casts for both the left ankle/leg and the right ankle/leg. Alternatively, the covers 170, 190 may have separate configurations for the left ankle/leg and the right ankle/leg.

It will be readily apparent to those skilled in the art that still further changes and modifications in the actual concepts described herein can readily be made without departing from the spirit and scope of the invention as defined by the following claims.

What is claimed is:

1. An orthopedic cast cover for covering an orthopedic cast of a user, comprising:
    a tubular portion for covering the orthopedic cast;
    a distal portion including a thumb hole for receiving a thumb of the user and an oval finger opening for receiving fingers of the user; and
    separate, spaced, parallel, elongated, linear, tubular finger separators spanning the oval finger opening between two opposite points on the circumference of the finger opening and adapted to extend between adjacent fingers in V-shaped portions formed between the fingers without surrounding the circumference of the fingers.

2. The method of claim 1, wherein the orthopedic cast cover has a configuration that fits both a left cast and a right cast.

3. The orthopedic cast cover of claim 1, wherein the orthopedic cast cover has a configuration that fits both a left cast and a right cast.

4. The orthopedic cast cover of claim 1, wherein the separators are absorbent.

5. The orthopedic cast cover of claim 1, wherein the orthopedic cast cover is a wrist orthopedic cast cover.

6. The orthopedic cast cover of claim 1, wherein the orthopedic cast cover is a short-arm orthopedic cast cover.

7. The orthopedic cast cover of claim 1, wherein the orthopedic cast cover is a long-arm orthopedic cast cover.

8. The orthopedic cast cover of claim 1, wherein the orthopedic cast cover includes inner and outer liners.

9. A method of using an orthopedic cast cover for covering an orthopedic cast of a user, the method comprising:
    providing an orthopedic cast cover including a tubular portion for covering the orthopedic cast, a distal portion including a thumb hole for receiving a thumb of the user and an oval finger opening for receiving fingers of the user, and separate, spaced, parallel, elongated, linear, tubular finger separators spanning the oval finger opening between two opposite points on the circumference of the finger opening and adapted to extend between adjacent fingers in V-shaped portions formed between the fingers without surrounding the circumference of the fingers;
    inserting at least one of an arm and wrist cast through the orthopedic cast cover so that the separate, spaced, parallel, elongated, linear, tubular finger separators extend between adjacent fingers in the V-shaped portions formed between the fingers of the user's hand without surrounding the circumference of the fingers; and
    absorbing moisture and soil in the V-shaped sections between the fingers with the separate, spaced, parallel, elongated, linear, tubular finger separators, thereby inhibiting development of skin lesions between the fingers.

10. The method of claim 9, further including multiple orthopedic cast covers, each with at least one of a unique color and design, and the method further includes removing the orthopedic cast cover from the arm or wrist cast, and replacing the orthopedic cast cover with a different orthopedic cast cover having a unique color and design.

11. The method of claim 9, wherein the orthopedic cast cover includes inner and outer liners.

12. The method of claim 9, wherein the orthopedic cast cover is a long-arm orthopedic cast cover, and inserting includes inserting a short-arm orthopedic cast through the orthopedic cast cover.

13. The method of claim 9, wherein the orthopedic cast cover is a short-arm orthopedic cast cover, and inserting includes inserting a short-arm orthopedic cast through the orthopedic cast cover.

14. The method of claim 9, wherein the separators are absorbent.

15. The method of claim 9, wherein the orthopedic cast cover is a wrist orthopedic cast cover, and inserting includes inserting a wrist cast through the orthopedic cast cover.

* * * * *